United States Patent [19]

Blythin

[11] Patent Number: 4,652,564
[45] Date of Patent: Mar. 24, 1987

[54] SUBSTITUTED SPIRO PYRIDINE DERIVATIVES AS ANTI-ALLERGY AND ANTIINFLAMMATORY AGENTS

[75] Inventor: David J. Blythin, North Caldwell, N.J.

[73] Assignee: Schering Corporation, Kenilworth, N.J.

[21] Appl. No.: 561,416

[22] Filed: Dec. 14, 1983

[51] Int. Cl.$^4$ .................. A61K 31/495; C07D 471/10
[52] U.S. Cl. .................................... 514/248; 514/242; 514/249; 514/258; 514/278; 544/182; 544/230; 546/18
[58] Field of Search .................. 546/18; 544/230, 182; 424/256, 250; 514/278, 248, 249, 258, 242

[56] References Cited

U.S. PATENT DOCUMENTS

Re. 26,655  8/1969  Sherlock et al. .................... 546/310

FOREIGN PATENT DOCUMENTS 52-64417  5/1977  Japan .................................... 514/278

OTHER PUBLICATIONS

Fournier, C. et al, *C. R. Acad. Sci.*, Paris, 1967, (69:CA 18992).
Fournier et al, *Bull. Soc. Chim.*, Fr. 68, 364–369.
Landis, J., *Mechanics of Patent Claim Drafting*, 2nd Ed., Practising Law Institute, New York, p. 120.
Rosenberg, P., *Patent Law Fundamentals*, vol. two, 2nd Ed., Clark Boardman, New York, 1985, p. 14–12.
Goodman and Gilman's, *The Pharmacological Basis of Therapeutics*, 6th Ed., MacMillan, New York, 1980, pp. 627, 629 and 1490.
*Chemical Abstracts*, 87:141,272y (1977), [Japan. Kokai 77 64,417, 5/27/77].

*Primary Examiner*—Richard A. Schwartz
*Attorney, Agent, or Firm*—James R. Nelson; Stephen I. Miller; Gerald S. Rosen

[57] ABSTRACT

Substituted spiro pyridine derivatives are anti-allergic and anti-inflammatory agents. They are also useful for the treatment of peptic ulcers.

Methods for their preparation and use are disclosed.

25 Claims, No Drawings

SUBSTITUTED SPIRO PYRIDINE DERIVATIVES AS ANTI-ALLERGY AND ANTIINFLAMMATORY AGENTS

BACKGROUND OF THE INVENTION

The production of a spiro[cyclopentane]quinolinedione is described in Chem. Pharm. Bull., 17, 1290 (1969). Several additional spiroquinoline diones are disclosed in Bull. Soc. Chim. Fr., 364 (1968). The references do not describe pharmaceutical uses for these compounds.

SUMMARY OF THE INVENTION

The invention sought to be patented in its chemical compound aspect is a compound having the structural formula I:

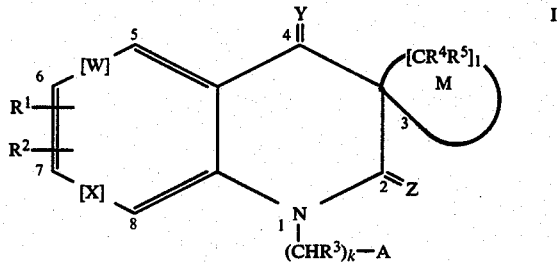

wherein
W and X may be the same or different and are CH or N;
Y and Z may be the same or different and are O or S;
$R^1$ and $R^2$ may be the same or different and are hydrogen, alkyl having from 1 to 6 carbon atoms, halogen, nitro, alkoxy having from 1 to 6 carbon atoms or trifluoromethyl;
$R^3$ is independently hydrogen or alkyl having from 1 to 6 carbon atoms;
$R^4$ and $R^5$ may be the same or different and are hydrogen or are from 1 to 7 alkyl groups each of which having from 1 to 6 carbon atoms;
the spiro ring, M, may contain one optional double bond;
k is 0, 1 or 2;
l is an integer of from 3 to 6; and
A is phenyl, naphthyl, indenyl, indanyl, phenanthridinyl, pyridinyl, pyrimidinyl, pyrazinyl, pyridazinyl, 1,2,4-triazinyl, furyl, thiophenyl, benzofuranyl, indolyl, imidazolyl, pyrazolyl, triazolyl, or thiazolyl any of which may be substituted with up to three of any of the following substituents, Q: hydroxy, alkyl having from 1 to 6 carbon atoms, halogen, nitro, alkoxy having from 1 to 6 carbon atoms, tri-fluoromethyl, cyano, cycloalkyl having from 3 to 7 carbon atoms, alkenyloxy having from 3 to 6 carbon atoms, alky-nyloxy having from 3 to 6 carbon atoms, $S(O)_m$—$R^a$ [wherein m is 0, 1 or 2 and $R^a$ is alkyl having from 1 to 6 carbon atoms], $NHSO_2R^a$ [wherein $R^a$ is defined herein], $NHSO_2CF_3$, $NHCOCF_3$, $SO_2NH_2$, $COR^b$ [wherein $R^b$ is OH, $NH_2$ or $OR^a$ (wherein $R^a$ is defined herein)], O—B—$COR^b$ [wherein B is alkylene having from 1 to 4 carbon atoms and $R^b$ is defined herein], or $NHCOR^c$ [wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having from 1 to 6 carbon atoms)].

In an embodiment of the invention k in formula I is zero. In another embodiment W is N and X is CH. In still other embodiments W is N in the 5- or 8-position, Y and Z are both oxygen, $R^1$ and $R^2$ are both hydrogen, and/or A is phenyl, pyridinyl, thiophenyl, triazolyl, imidazolyl or thiazolyl any of which may be substituted with up to three substituents Q as described above. In yet another embodiment the letter l in the M spiro ring represents 4, 5 or 6 and the ring M may contain up to four (e.g., up to two) $R^4$ and $R^5$ groups each of which may be the same or different and are hydrogen or alkyl having from 1 to 6 carbon atoms, e.g., $R^4$ and $R^5$ may be hydrogen, methyl, ethyl, propyl, n-propyl, n-butyl or iso-butyl.

A preferred subgenus of compounds is that wherein Y and Z are both oxygen.

An additional preferred subgenus of compounds is represented by the structural formula II:

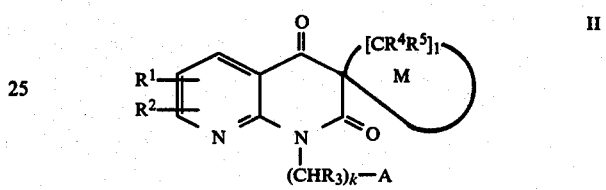

wherein $R^1$, $R^2$, $R^3$, $R^4$, $R^5$, M, A, k and l are defined herein.

An additional preferred subgenus of compounds is represented by the structural formula III:

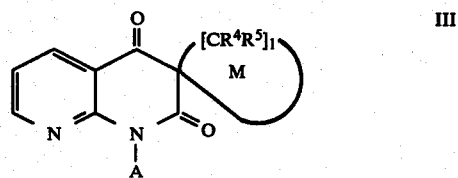

wherein $R^4$, $R^5$, M, A and l are defined herein.

One group of compounds of the invention are represented by the formula V

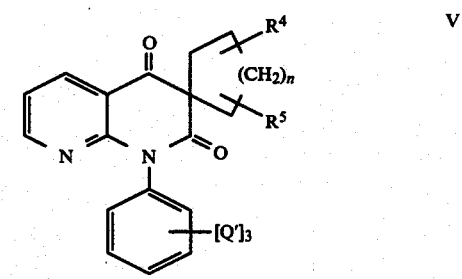

wherein n is 1, 2 or 3; $R^4$ and $R^5$ are hydrogen, methyl or ethyl; and each Q' is independently selected from hydrogen, hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_m$—$R^a$ {wherein m is 0, 1 or 2 and $R^a$ is alkyl having from 1 to 6 carbon atoms}, $NHSO_2R^a$ {wherein $R^a$ is defined herein}, $NHSO_2CH_3$, $NHCOCF_3$, $SO_2NH_2$, $COR^b$ {wherein $R^b$ is OH, $NH_2$ or $OR^a$ (wherein $R^a$ is defined herein)}, O—B—$COR^b$ {wherein B is alkylene having from 1 to 4 carbon atoms and $R^b$ is defined herein}, or $NHCOR^c$ {wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having from 1 to 6 carbon atoms)}.

The invention sought to be patented in its pharmaceutical composition aspect is a pharmaceutical composition which comprises a compound having structural formula I in combination with a pharmaceutically acceptable carrier.

The invention sought to be patented in a first pharmaceutical method aspect is a method for treating allergic reactions in a mammal which comprises administering an anti-allergic effective amount of the above-defined pharmaceutical composition to said mammal.

The invention sought to be patented in a second pharmaceutical method aspect is a method for treating inflammation in a mammal which comprises administering an anti-inflammatory effective amount of the above-defined pharmaceutical composition to said mammal.

The invention sought to be patented in a third pharmaceutical method aspect is a method for treating peptic ulcers in a mammal which comprises administering a cytoprotective effective amount of the above defined pharmaceutical composition to said mammal.

DESCRIPTION OF THE INVENTION

The compounds of the invention may be prepared from a properly substituted compound having the structural formula IV

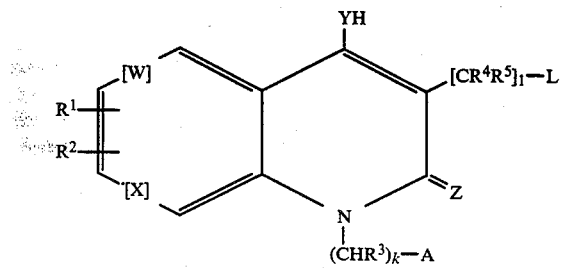

wherein W, X, Y, Z, $R^1$, $R^2$, $R^3$, $R^4$, $R^5$, k and l are as defined herein, and L is a substituent known to those skilled in the art as a "leaving group."

Treatment of compound IV with an organic base such as triethylamine or 1,8-diazabicyclo[5.4.0]undec-7-ene, DBU [Angew. Chem., Internat. Ed., 6 76 (1967)]in a nonreactive solvent such as methylene chloride will produce the compounds of the invention having structural formula I.

For purposes of the invention a "leaving group" is defined as a substituent which may be displaced and carry a negative charge. Examples of such substituents are bromide, iodide, trifluoroacetoxy, p-toluene-sulfonyloxy, methanesulfonyloxy and the like. The preferred leaving group is bromide.

The compounds having structural formula IV wherein L is OH may be prepared by known methods from known starting materials.

Exemplary of such starting materials for preparing compounds having structural formula IV are 2-anilino nicotinic acids which may be prepared, for example, as described in U.S. Pat. No. Re. 26,655; and 2-phenylamino-3-pyrazine carboxylate esters which may be prepared substantially as exemplified herein starting with a 2-amino-3-pyrazine carboxylate ester. 2-Anilino-3-pyrazine carboxylic acid is a known compound, C.A., 75, 20154e (1971), which may be esterified by standard procedures.

Compounds having structural formula IV wherein L is bromine may be prepared, for example, from the corresponding hydroxy compound by treatment with concentrated HBr (e.g. 48% HBr). Other desired leaving group substituents, L, may be prepared by known methods.

The compounds having structural formula I wherein Y and/or Z are oxygen may be converted to the corresponding compound wherein Y and Z are sulfur by known methods. For example treatment with Lawesson's Reagent [2,4-bis(4-methoxyphenyl)-1,3-dithia-2,4-diphosphetane-2,4-disulfide]in hot toluene will effect this conversion.

When utilized herein and in the appended claims the below listed terms, unless specified otherwise, are defined as follows:

halogen—fluorine, chlorine, bromine and iodine;

alkyl and alkoxy—comprised of straight and branched carbon chains containing from 1 to 6 carbon atoms;

alkenyloxy—comprised of straight and branched carbon chains containing from 3 to 8 carbon atoms and comprising a carbon to carbon double bond; and alkynyloxy—comprised of straight and branched carbon chains containing from 3 to 8 carbon atoms and comprising a carbon to carbon triple bond.

Certain of the compounds of the invention may contain a double bond in the spiro ring, M. Those skilled in the art will recognize that such a double bond may not involve the "spiro" carbon atom, i.e. the 3-carbon atom identified in structural formula I.

The compounds of the invention are comprised of a —$(CHR^3)_k$— substituent wherein the $R^3$ group may vary independently. Thus, for example, when k equals 2 the following patterns of substitution (wherein $CH_3$ is used to represent any substituent, $R^3$,) are contemplated: —$CH_2CH(CH_3)$—, —$CH(CH_3)CH_2$—, —$[C(CH_3)H]_2$— and the like. In addition when k equals 2, substituents such as —$CH(CH_3)CH(C_2H_5)$—, —CH-(i—$C_3H_7)CH(C_2H_5)$—are also contemplated.

Certain compounds of the invention may contain up to 3 substituents, Q. When more than one such substituent, Q, is present they may be either the same or different.

Certain compounds of the invention may exist in isomeric forms. The invention contemplates all such isomers both in pure form and in admixture, including racemic mixtures.

The compounds of this invention can be used to treat allergy caused diseases and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The anti-allergy method of this invention is identified by tests which measure a compound's inhibition of anaphylactic bronchospasm in sensitized guinea pigs having antigen induced broncho-constriction. For example, the compound 1'-(phenyl)spiro[cyclopentane-1,3'-(1,8)naphthyridine]-2',4'-(1'H)-dione was found to inhibit anaphylactic bronchospasms in such test procedure when given at an oral dose of 10 mg/kg. Said compound was also found to inhibit allergen-induced histamine release from guinea pig and human sensitized tissue. The compounds are effective non-adrenergic, non-anticholinergic antianaphylactic agents. When administered orally they are active at doses from about 0.1 to 10 mg/kg of body weight; when administered parenterally, e.g., intravenously, the compounds are active at dosages of from about 0.05 to 5 mg/kg body weight; when administered by inhalation (aerosol or nebulizer) the compounds are active at dosages of about 0.25 to 5 mg per puff, one to four puffs may be taken every 4 hours.

The compounds of this invention are also useful for the treatment of inflammation; thus, they are useful for the treatment of: arthritis, bursitis, tendonitis, gout and other inflammatory conditions. The antiinflammatory use of the compounds of the present invention may be demonstrated by the Reversed Passive Arthus Reaction (RPAR) Synovitis technique as set forth below using male Lewis rats (obtained from Charles River Breeding Laboratories) weighing 200-250 grams. The potency of the compounds is determined using indomethacin as the standard. On the basis of the test results, an oral dosage range of about 5 milligrams per kilogram of body weight per day to about 50 milligrams per kilogram of body weight per day in divided doses taken at about 4 hour intervals is recommended.

The dosage to be administered and the route of administration depends upon the particular compound used, the age and general health of the patient and the severity of the inflammatory condition. Thus, the dose ultimately decided upon must be left to the judgment of a trained health-care practitioner.

RPAR Synovitis Technique

A Lewis rat is dosed orally with drug or placebo one hour prior to intravenous administration of 2.28 mg of bovine serum albumin (BSA) in 0.2 cc of pyrogen-free saline followed by the intraarticular injection of 0.54 mg of rabbit anti-BSA antibody in 0.03 cc of pyrogen-free saline into one knee joint. The contralateral knee is injected with 0.03 cc of pyrogen free saline. All injections are made with the animal under light ether anesthesia. Three hours later the rat is again dosed orally with drug or placebo. All drug doses are split. That is, one-half of the dose is administered before lesion induction and one-half is administered after lesion induction.

The following morning (about 17 hours after lesion induction) the rat is killed and both knee joints are exposed. The subpatellar areolar tissue with attendant synovium is excised and weighed. Differences between the weight of antibody and saline injected knees are considered to represent the inflammatory response for each animal (delta synovial weight). Differences in delta synovial weight between lesion controls and drug-treated rats are evaluated for statistical significance with an analysis of variance. Relative potencies are determined with a linear regression analysis.

The compounds of this invention are also useful in the treatment of peptic ulcers. They display chemotherapeutic activity which enables them to relieve the symptoms of peptic ulcer disease, stress ulceration, and promote healing of gastric and/or duodenal ulcers. The antiulcer activity of the compounds of this invention is identified by tests which measure the cytoprotective effect in rats. The compounds are also useful as conjunctive therapeutic agents for coadministration with such antiinflammatory/analgesic agents as aspirin, indomethacin, phenylbutazone, ibuprofen, naproxen, tolmetin and other agents. The compounds of this invention prevent the untoward side effects of irritation and damage to the gastrointestinal tract caused by such agents.

The compounds of this invention are evaluated for their antiulcer activity characteristics by standard biological testing procedures.

In cytoprotective tests in rats in which ethanol is employed to induce gastrointestinal damage, the compounds of this invention are found to be effective at doses of about 0.05-50 mg/kg of body weight per day. Preferably the total dosages are administered in 2-4 divided doses per day.

When administered parenterally, e.g. intravenously, the compounds are administered at a dosage range of about 0.01-10 mg/kg of body weight in single or multiple daily doses.

To treat peptic ulcer disease, and prevent and treat drug-induced gastric ulceration, the active compounds of this invention can be administered in unit dosage forms such as tablets, capsules, pills, powders, granules, sterile parenteral solutions or suspensions, suppositories, mechanical delivery devices, e.g. transdermal, and the like.

The compounds of the invention of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

PREPARATIVE EXAMPLE 1

4-Hydroxy-3-(4-hydroxybutyl)-1-phenyl-1,8-naphthyridin-2(1H)-one

A mixture of methyl 2-phenylamino-nicotinate (100 g.), ε-caprolactone (1000 g.) and potassium t-butoxide (200 g.) was stirred at room temperature, in a nitrogen atmosphere, for ½ hr. It was heated at 45° C. for 1 hr. then at 85° C. for 2 hrs. and finally at 105° C. for 3 hr.

The hot mixture was poured carefully into 8 L of 5% KOH solution and was stirred overnight.

The mixture was extracted with 2 L of ether and the aqueous phase was retained. It was extracted again with a fresh 2 L of ether. The clear aqueous phase was adjusted to pH 4.5 with conc. HCl to yield a white solid which was filtered off, washed with water and dried to yield 4-hydroxy-3-(4-hydroxybutyl)-1-phenyl-1,8-naphthyridin-2(1H)-one, m.p. 205.5°–206.5° C. (from isopropanol).

By substituting the relevant ester and lactone in this preparative example intermediates to many other compounds of the invention may be prepared.

PREPARATIVE EXAMPLE 2

(3-hydroxypropyl)-1-phenyl-1,8-naphthyridin-2(1H)one

Methyl 2-phenylamino-nicotinate (25 g.) was dissolved in δ-valerolactone (240 g.) with stirring in an atmosphere of nitrogen. To the resulting solution was added potassium t-butoxide (50 g.) and the mixture was stirred at room temperature for ½ hr. It was then heated to 100° C. for 3 hr. after which time it was poured into 1 L of 5% NaOH solution and stirred overnight.

The mixture was extracted (2x) with 1L of ether then the aqueous layer was adjusted to pH 4.5 with conc. HCl. The solid which separated was filtered off, washed with water and dried to yield 4-hydroxy-3-(3-hydroxypropyl)-1- phenyl-1,8-naphthyridin-2(1H)-one, m.p. 218°–220° C.

By utilizing the correspondingly substituted starting materials in the procedures of preparative examples 1 or 2, the following compounds were obtained:
1-(4-chlorophenyl)-4-hydroxy-3-(3-hydroxypropyl)-1,8-naphthyridin-2(1H)one, m.p. 249.5°–251° C.;
4-hydroxy-3-(3-hydroxypropyl)-1-(4-methylphenyl)-1,8-naphthyridin-2(1H)one, m.p. 227°–228° C.;
4-hydroxy-3-(3-hydroxypropyl)-1-(4-methoxyphenyl)-1,8-naphthyridin-2(1H)one, m.p. 229°–231° C.;
1-(3,4-dichlorophenyl)-4-hydroxy-3-(3-hydroxypropyl)-1,8-naphthyridin-2(1H)one, m.p. 230°–232° C.;
1-(4-chlorophenyl)-4-hydroxy-3-(4-hydroxybutyl)-1,8-naphthyridin-2(1H)one, m.p. 238°–240° C.;
4-hydroxy-3-(4-hydroxybutyl)-1-(4-methylphenyl)-1,8-naphthyridin-2(1H)one, m.p. 186°–188° C.;
4-hydroxy-3-(4-hydroxybutyl)-1-(4-methoxyphenyl)-1,8-naphthyridin-2(1H)one, m.p. 237°–239° C.;
1-(3,4-dichlorophenyl)-4-hydroxy-3-(4-hydroxybutyl)-1,8-naphthyridin-2(1H)one, m.p. 188°–190° C.;
1-(3-chlorophenyl)-4-hydroxy-3-(4-hydroxybutyl)-1,8-naphthyridin-2-(1H)one, m.p. 176°–178° C.;
4-hydroxy-3-(4-hydroxybutyl)-1-(3-methoxyphenyl)-[1,8]-naphthyridin-2(1H)-one, m.p 217°–219° C.;
4-hydroxy-3-(4-hydroxybutyl)-1-phenyl-quinolin-2(1H)-one, m.p. 165.5°–158° C.

PREPARATIVE EXAMPLE 3

Ethyl 5-(4-hydroxy-2-oxo-1-phenyl-1H-[1,8]naphthyridin-3-yl)pentanoate

Methyl 2-phenylaminonicotinate (8.5 g.) was dissolved with stirring in diethyl pimelate (80 ml.) in an atmosphere of nitrogen. To the mixture was added potassium t-butoxide (13 g.) and the mixture was stirred at room temperature for 1 hr. It was then heated to 135°–140° C. for 6 hours after which time it was poured into water. The aqueous layer was extracted with methylene chloride and then adjusted to pH 4.5 with conc. HCl. Solid sodium chloride was added after which the solid was filtered off, washed with water and dried, m.p. 168°–169° C.

By substituting diethyl suberate for diethylpimelate in the above procedure; ethyl 6-(4-hydroxy-2-oxo-1-phenyl-1H-[1,8]naphthyridin-3-yl)hexanoate, m.p. 167°–168° C. was obtained

PREPARATIVE EXAMPLE 4

4-Hydroxy-3-(5-hydroxypentyl)-1-phenyl-1,8-naphthyridin-2(1H)one

To a suspension of ethyl 5-(4-hydroxy-2-oxo-1-phenyl-1H-[1,8]-naphthyridin-3-yl)pentanoate (1 g.) (prepared as in preparative example 3) in dry dioxane (50 ml.) in an atmosphere of nitrogen is added lithium borohydride (0.34 g.). The mixture is stirred at room temperature for 20 min. then it is heated to 60° C. for 16 hrs.

The product is poured into water, adjusted to pH 4.5 with acetic acid and the resulting solid is filtered off. The solid is washed with water and dried to yield 4-hydroxy-3-(5-hydroxypentyl)-1-phenyl-1,8-naphthyridin-2-(1H)-one.

PREPARATIVE EXAMPLE 5

3-(4-Bromobutyl)-4-hydroxy-1-phenyl-1,8-naphthyridin-2(1H)one

In 47% HBr (100 ml.) was dissolved 4-hydroxy-3-(4-hydroxybutyl)-1-phenyl-1,8-naphthyridin-2(1H)-one (5 g) in an atmosphere of nitrogen at room temperature. After 1 hr. the solution was heated to 90° C. and it was kept there for 6 hrs.

After cooling, the product was poured into 1L of H₂O and the pH was adjusted to 5 with potassium acetate. After stirring for 5 minutes, the solid was filtered off, washed with water and dried to yield 3-(4-bromobutyl)-4-hydroxy-1-phenyl-1,8-naphthyridin-2(1H)-one, m.p. 194°–196° C.

By substituting the appropriate starting materials and using the procedure as above, the following additional compounds were obtained:
3-(4-bromobutyl)-4-hydroxy-1-(3,4-dichlorophenyl)-1,8-naphthyridin-2(1H)one, m.p. 169°–171° C.;
3-(4-bromobutyl)-4-hydroxy-1-(4-chlorophenyl)-1,8-naphthyridin-2(1H)one, m.p. 228°–230° C.;
3-(4-bromobutyl)-1-(3-hydroxyphenyl)-4-hydroxy-1,8-naphthyridin-2(1H)one, m.p. 214°–216° C.;
3-(4-bromobutyl)-1-(3-methoxyphenyl)-4-hydroxy-1,8-naphthyridin-2(1H)one, m.p. 179.5°–181° C.;
3-(4-bromobutyl)-1-(3-chlorophenyl)-4-hydroxy-1,8-naphthyridin-2(1H)one, m.p. 195.5°–197° C.; and
3-(4-bromobutyl)-4-hydroxy-1-phenyl-quinolin-2(1H)one, m.p. 206.5°–208° C.

PREPARATIVE EXAMPLE 6

Methyl-2-phenylamino-3-pyrazine carboxylate (A) Methyl 2-bromo-3-pyrazine carboxylate To a stirred mixture of 12.7 g. of methyl 2-amino pyrazine carboxylate and 47 ml. of 48% hydrobromic acid there was added, dropwise, 12.6 ml. of bromine keeping the temperature at 0°. A solution of 14.4 g. of sodium nitrite in 60 ml. of water was then added, dropwise, at 0° and the reaction mixture stirred for 15 minutes. The reaction mixture was basified to pH 8 with sodium bicarbonate and extracted with ethyl acetate and again with chloroform. The organic layers were dried over magnesium sulfate, filtered and concentrated to a yellow oil. Recrystallization from ether-hexane yielded the product, m.p. 43°–45° C.

(B) Methyl 2-phenylamino-3-pyrazine carboxylate:

A mixture of 9.5 g. of methyl 2-bromo-3-pyrazine carboxylate, 8.2 g. of aniline, 0.5 g. of p-toluene sulfonic acid and 100 ml. of water was stirred and refluxed for two hours. The reaction mixture was poured on ice, extracted with ethyl acetate, the organic extracts were dried and concentrated to yield an oil. The crude residue was eluted on a silica gel column with ethyl acetate-hexane (1:2) yielding the product of this example as a yellow solid, m.p. 72°–75° C.

PREPARATIVE EXAMPLE 7

3-(2-Hydroxyethyl)-4-hydroxy-1-phenyl-1,8-naphthyridin-2(1H)one

To a solution of 6.8 g. of methyl 2-phenylamino-3-pyridine carboxylate in 60 ml. of gamma-butyrolactone there was added, under nitrogen, 13.4 g. of potassium tertiary butoxide. The reaction mixture was heated and stirred for one hour at 95° C., poured on ice and stirred overnight. The mixture was extracted with ether, the aqueous layer acidified with acetic acid to pH 4.5 and the product was collected by filtration. Recrystallization from chloroform, acetone, isopropanol yielded the product of this example as a colorless solid; m.p. 235°–236° C.

PREPARATIVE EXAMPLE 8

3,9-Dihydro-9-phenyl-furo[2,3-b][1,8]-naphthyridin-4(2H)-one

A solution of 4-hydroxy-3-(2-hydroxyethyl)-1-phenyl-1,8-naphthyridin-2(1H)-one in Eaton's Reagent (10% P₂O₅ in methane sulfonic acid; 40 ml.) was stirred in an atmosphere of nitrogen and was heated to 70° C. for 2 hr. After cooling, the product was poured into water, adjusted to pH 4 with NaHCO₃, filtered, washed with water, air dried and recrystallized from isopropanol with decolorization to yield the product, m.p. 245°–247° C.

EXAMPLE 1

1'-Phenylspiro[cyclopentane-1,3'-(1,8)-naphthyridine]-2',4'-(1'H)dione

A suspension of 3-(4-bromobutyl)-4-hydroxy-1-phenyl-1,8-naphthyridin-2(1H)one (5 g.) in methylene chloride (350 ml.), in an atmosphere of nitrogen, was stirred at room temperature and to it was added triethylamine (4.1 ml.). The mixture was stirred at room temperature for 16 hrs. Water (300 ml.) was added and the aqueous layer was adjusted to pH 4.5 with hydrochloric acid.

The organic layer was separated and the aqueous layer was back-extracted with methylene chloride. The combined organic layers were washed with water, dried ($Na_2SO_4$), filtered and evaporated to yield a solid which was recrystallized from isopropanol to yield 1'-phenyl-spiro[cyclopentane-1,3'-(1,8)naphthyridine]-2',4'-(1'H)dione, m.p. 178°–179° C.

By utilizing the appropriately substituted starting materials in the above-described procedure, the following products were obtained:

1'-(4-methylphenyl)spiro[cyclopentane-1,3'-(1,8)naph-thyridine]-2',4'-(1'H)-dione, m.p. 177°–179.5° C.;
1'-(4-chlorophenyl)spiro[cyclopentane-1,3'-(1,8)naph-thyridine]-2',4'-(1'H)-dione, m.p. 181.5°–183° C.;
1'-(3,4-dichlorophenyl)spiro[cyclopentane-1,3'-(1,8)naphthyridine]-2',4'-(1'H)-dione, m.p. 143°–145.5° C.;
1'-(3-chlorophenyl)spiro[cyclopentane-1,3'-(1,8)naph-thyridine]-2',4'-(1'H)-dione, m.p. 165° C.;
1'-(3-methoxyphenyl)spiro[cyclopentane-1,3'-(1,8)naphthyridine]-2',4'-(1'H)-dione, m.p. 159°–160.5° C.;
1'-(3-hydroxyphenyl)spiro[cyclopentane-1,3'-(1,8)naph-thyridine]-2',4'-(1'H)-dione, m.p. 218°–220° C.;
1'-phenylspiro[cyclopentane-1,3'-quinoline]-2',4'-(1'H)dione, m.p. 166°–168° C.

In general, by following the procedures described in Preparative Examples 1, 4, 5 or 6, or an art-recognized modification thereof, using lactones with desired substituents, other intermediates, II (B=O), may be prepared which are useful for preparing products of the invention by the method of Example 1.

EXAMPLE 2

1'-Phenylspiro[cyclohex-3-ene]-1,3'-[1,8]naphthyridine]-2'4'-(1'H)dione

A.
4-Hydroxy-3-(5-hydroxy-3-pentynyl)-1-phenyl-1,8-naphthyridin-2(1H)-one.

A solution of 3,9-dihydro-9-phenyl-furo[2,3-b][1,8]naphthyridin-4[2H]-one (prepared as in Preparative Example 8) in dimethylsulfoxide/tetrahydrofuran(DMSO/THF) is stirred and cooled to ca. 0° C. while to it is added a pre-formed solution of the sodium salt of the tetrahydropyranyl (THP) ether of propargyl alcohol $Na^+ - C \equiv C - CH_2 - O - THP$) which is prepared from the THP ether of propargyl alcohol and an equivalent amount of dimsyl sodium in DMSO/THF. Dimsyl sodium is prepared by refluxing the desired amount of sodium hydride in DMSO/THF (1:10) until reaction is complete.

The reaction is allowed to warm up until reaction is observed, (monitor by t.l.c.). When complete reaction is observed, (monitor by t.l.c.). When complete the reaction is made sufficiently acidic to remove the protecting group, and the product is isolated.

B.
(Z)-4-Hydroxy-3-(5-hydroxy-3-pentenyl)-1,8-naphthyridin-2(1H) one

The acetylene (from part A) is dissolved in methanol containing 2% by weight (of the acetylene) of 5% palladium on barium sulfate which also contains pure quinoline in amount equal to the weight of the catalyst. The mixture is hydrogenated at atmospheric pressure until one equivalent of hydrogen is taken up. Filtration and evaporation produces the product.

C. 1'-Phenyl spiro[(cyclohex-3-ene)-1,3'[1,8]-naphthyridine]-2',4'-(1'H)-dione The cis-olefin (from part B) is dissolved/suspended in pyridine at 0° C. A slight excess of mesyl chloride (1.05 equivalents) is added and the mixture is stirred until reaction is complete (monitor by t.l.c.). The pyridine is removed under high vacuum and the residue is dissolved in $CH_2Cl_2$. The solution is washed with a small volume of cold water, dried, and treated with an excess (1.2 equivalents) of triethylamine. When reaction is complete the crude product is isolated by washing the $CH_2Cl_2$ with water, evaporation and chromatography in $CH_3CN:H_2O$ (80:20) over reversed-phase silica (Whatman Partisil (40; ODS-3), yields the product.

I claim:

1. A compound having the structural formula I:

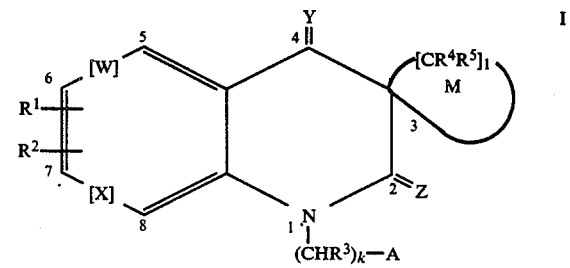

wherein

W and X may be the same or different and are CH or N;

Y and Z may be the same or different and are O or S;

$R^1$ and $R^2$ may be the same or different and are hydrogen, alkyl having from 1 to 6 carbon atoms, halogen, nitro, alkoxy having from 1 to 6 carbon atoms or trifluoromethyl;

each $R^3$ is independently hydrogen or alkyl having from 1 to 6 carbon atoms;

$R^4$ and $R^5$ may be the same or different and are hydrogen or are from 1 to 7 alkyl groups each of which having from 1 to 6 carbon atoms:

the spiro ring, M, may contain one optional double bond;

k is 0, 1 or 2;

l is an integer of from 3 to 6; and

A is phenyl which may be optionally substituted with up to three of any of the following substituents, Q: hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_m—R^a$ {wherein m is 0, 1 or 2 and $R^a$ is alkyl having from 1 to 6 carbon atoms}, $NHSO_2R^a$ {wherein $R^a$ is defined herein}, $NHSO_2CF_3$, $NHCOCF_3$, $SO_2NH_2$, $COR^b$ {wherein $R^b$ is OH, $NH_2$ or $OR^a$ (wherein $R^a$ is defined herein)}, $O—B—COR^b$ {wherein B is alkylene having from 1 to 4 carbon atoms and $R^b$ is defined herein}, or $NHCOR^c$ {wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or NHR$^e$ (wherein R$^e$ is hydrogen or alkyl having from 1 to 6 carbon atoms)}.

2. A compound defined in claim 1 wherein k is 0.

3. A compound defined in claim 2 wherein W is N and X is CH.

4. A compound defined in claim 3 wherein Y and Z are both oxygen.

5. A compound defined in claim 4 wherein R$^1$ and R$^2$ are both hydrogen.

6. A compound defined in claim 5 wherein W is situated in the 5- or 8- position.

7. A compound defined in claim 6 wherein W is situated in the 8- position.

8. A compound having the structural formula I:

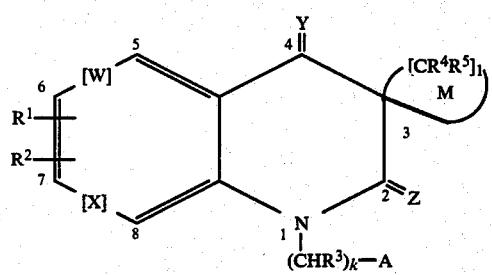

wherein
W and X may be the same or different and are CH or N;
Y and Z may be the same or different and are O or S;
R$^1$ and R$^2$ may be the same or different and are hydrogen, alkyl having from 1 to 6 carbon atoms, halogen, nitro, alkoxy having from 1 to 6 carbon atoms or trifluoromethyl;
R$^3$ is independently hydrogen or alkyl having from 1 to 6 carbon atoms;
R$^4$ and R$^5$ may be the same or different and are hydrogen or are from 1 to 7 alkyl groups each of which having from 1 to 6 carbon atoms;
the spiro ring, M, may contain one optional double bond;
k is 0, 1 or 2;
l is an integer of from 3 to 6; and
A is phenyl, naphthyl, indenyl, indanyl, phenanthridinyl, pyridinyl, pyrimidinyl, pyrazinyl, pyridazinyl, 1,2,4-triazinyl, furyl, thiophenyl, benzofuranyl, indolyl, imidazolyl, pyrazolyl, triazolyl or thiazolyl any of which may be substituted wiht up to three of any of the following substituents, Q: hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, S(O)$_m$—R$^a$ {wherein m is 0, 1 or 2 and R$^a$ is alkyl having from 1 to 6 carbon atoms}, NHSO$_2$R$^a$ {wherein R$^a$ is defined herein}, NHSO$_2$CF$_3$, NHCOCF$_3$, SO$_2$NH$_2$, COR$^b$ {wherein R$^b$ is OH, NH$_2$ or OR$^a$ (wherein R$^a$ is defined herein)}, O—B—COR$^b$ {wherein B is alkylene having from 1 to 4 carbon atoms and R$^b$ is defined herein}, or NHCOR$^c$ {wherein R$^c$ is hydrogen, alkyl having from 1 to 6 carbon atoms, alkoxy having from 1 to 6 carbon atoms, COR$^d$ (wherein R$^d$ is hydroxy or alkoxy having from 1 to 6 carbon atoms) or NHR$^e$ (wherein R$^e$ is hydrogen or alkyl having from 1 to 6 carbon atoms)}.

9. A compound defined in claim 8 wherein A is phenyl, pyridinyl, thiophenyl, triazolyl, imidazolyl or thiazolyl any of which may be substituted with up to 3 substituents, Q, as defined in claim 1.

10. A compound defined in claim 9 wherein l is 4, 5 or 6.

11. A compound defined in claim 10 which may contain up to 4 R$^4$ and R$^5$ groups each of which may be the same or different and are hydrogen or alkyl having from 1 to 6 carbon atoms.

12. A compound defined in claim 11 wherein R$^4$ and R$^5$ are hydrogen, methyl, ethyl, propyl, iso-propyl, n-butyl or iso-butyl.

13. A compound defined in claim 9 which may contain up to 2 R$^4$ and R$^5$ groups each of which may be the same or different and are hydrogen or alkyl having from 1 to 6 carbon atoms.

14. A compound defined in claim 13 wherein R$^4$ and R$^5$ are hydrogen, methyl or ethyl.

15. A compound defined in claim 8 having the structural formula II

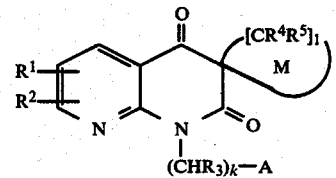

16. A compound defined in claim 8 having the structural formula III

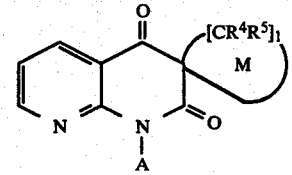

17. A compound having the structural formula V:

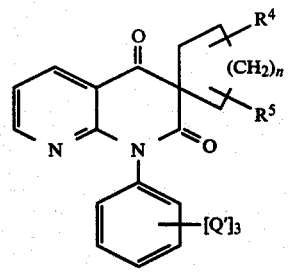

wherein n is 1, 2 or 3; R$^4$ and R$^5$ are hydrogen, methyl or ethyl and each Q' is independently selected from hydrogen, hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, S(O)$_m$—R$^a$ {wherein m is 0, 1 or 2 and R$^a$ is alkyl having from 1 to 6 carbon atoms}, NHSO$_2$R$^a$ {wherein R$^a$ is defined herein}, NHSO$_2$CF$_3$, NHCOCF$_3$, SO$_2$NH$_2$, COR$^b$ {wherein R$^b$ is OH, NH$_2$ or OR$^a$ (wherein R$^a$ is defined herein)}, O—B—COR$^b$ {wherein B is alkylene having from 1 to 4 carbon atoms and R$^b$ is defined herein}, or NHCOR$^c$ {wherein R$^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having from 1 to 6 carbon atoms)}.

18. A compound having the name 1'-(3-chlorophenyl)spiro [cyclopentane-1,3'-)1,8)-naphthyridine]-2',4'-(1'H)-dione.

19. A compound having the name:

1'-phenylspiro [cyclopentane-1,3'- (1,8) naphthyridine]-2',4'-(1'H)-dione;
1'-(4-methylphenyl)spiro[cyclopentane-1,3'-(1,8)naphthyridine]-2',4'-(1'H)-dione;
1'-(4-chlorophenyl)spiro[cyclopentane-1,3'-(1,8)naphthyridine]-2',4'-(1'H)-dione;
1'-(3,4-dichlorophenyl)spiro[cyclopentane-1,3'-(1,8)naphthyridine]-2',4'-(1'H)-dione;
1'-(3-chlorophenyl)spiro[cyclopentane-1,3'-(1,8)naphthyridine]-2',4'-(1'H)-dione;
1'-(3-methoxyphenyl)spiro[cyclopentane-1,3'-(1,8)naphthyridine]-2',4'-(1'H)-dione;
1'-(3-hydroxyphenyl)spiro[cyclopentane-1 3'-(1,8) naphthyridine]-2',4'-(1'H)-dione; and
1'-phenylspiro[cyclopentane-1,3'-quinoline]-2',4'-(1'H)dione.

20. A pharmaceutical composition for treating allergic reactions comprising an anti-allergic effective amount of a compound as defined in claim 1 in combination with a pharmaceutically acceptable carrier.

21. A pharmaceutical composition for treating inflamation comprising an anti-inflammatory effective amount of a compound as defined in claim 1 in combination with a pharmaceutically acceptable carrier.

22. A pharmaceutical composition for treating peptic ulcers comprising a cytoprotective effective amount of a compound as defined in claim 1 in combination with a pharmaceutically acceptable carrier.

23. A method for treating allergic reactions in a mammal which comprises administering an anti-allergic effective amount of the pharmaceutical composition defined in claim 20 to said mammal.

24. A method for treating inflammation in a mammal which comprises administering an anti-inflammatory effective amount of the pharmaceutical composition defined in claim 21 to said mammal.

25. A method for treating peptic ulcers in a mammal which comprises administering a cytoprotective effective amount of the pharmaceutical composition defined in claim 22 to said mammal.

* * * * *